United States Patent [19]

Bruylants et al.

[11] Patent Number: 4,479,024

[45] Date of Patent: Oct. 23, 1984

[54] STYRENE FROM TOLUENE AND FORMALDEHYDE

[75] Inventors: Philippe M. Bruylants, Ekersen, Belgium; Robert L. Garten, Cupertino, Calif.

[73] Assignee: Ashland Oil, Inc., Ashland, Ky.

[21] Appl. No.: 500,039

[22] Filed: Jun. 1, 1983

[51] Int. Cl.$^3$ .............................................. C07C 3/52
[52] U.S. Cl. .................................. 585/437; 585/438; 502/340; 502/344
[58] Field of Search ............... 585/437, 435, 436, 438; 502/340, 344

[56] References Cited

U.S. PATENT DOCUMENTS

| | | | |
|---|---|---|---|
| 3,494,969 | 2/1970 | Kauos et al. ...................... | 570/200 |
| 3,766,288 | 10/1973 | Shima et al. ...................... | 585/438 |
| 3,816,432 | 6/1974 | Franz ................................. | 585/438 |
| 3,954,895 | 5/1976 | Shima et al. ...................... | 585/438 |
| 4,115,424 | 9/1978 | Unland et al. ..................... | 585/438 |
| 4,140,726 | 2/1979 | Unland et al. ..................... | 585/438 |

FOREIGN PATENT DOCUMENTS

| | | | |
|---|---|---|---|
| 6008930 | 12/1970 | Japan ................................. | 585/438 |
| 6008932 | 3/1971 | Japan ................................. | 585/438 |
| 4808732 | 6/1971 | Japan ................................. | 585/438 |
| 1004127 | 6/1974 | Japan ................................. | 585/438 |
| 639845 | 10/1976 | U.S.S.R. ........................... | 585/438 |

OTHER PUBLICATIONS

Yashima et al., J. Catalysis, 26, 303, (1972).

Primary Examiner—Delbert E. Gantz
Assistant Examiner—A. Pal
Attorney, Agent, or Firm—Robert J. Grassi

[57] ABSTRACT

Toluene and formaldehyde produce styrene in a gas phase catalytic process using a basic hydroxide of Group I or II, at formaldehyde to toluene mole ratios of from 0.001 to 0.10.

4 Claims, No Drawings

STYRENE FROM TOLUENE AND FORMALDEHYDE

BACKGROUND OF THE INVENTION a. Field of the Invention

The invention pertains to the catalytic production of styrene from toluene and formaldehyde.

b. Description of the Prior Art

Production of styrene from toluene and formaldehyde is important because styrene is a large volume commodity chemical, and toluene and formaldehyde are low cost sources of reactants.

Japanese Patent No. 52-133932(1977) and K. Tanabe et al *React Kin Catal Lett*. Vol. 7 347 (1977) describe the formation of styrene by reaction of toluene and methanol over alkali and alkaline earth metal oxides and hydroxides. But the process is not commercially useful because large amounts of ethylbenzene are produced as a co-product, which is expensive to separate from the styrene. Other catalytic processes use the alkali and alkaline earth metal substituted crystalline aluminosilicates, (see) Y. N. Sidorenko et al, *Dokl. Akad. Nauk*, USSR 173 132 (1967); and T. Yashima et al, *J. Catal* 26 303 (1972). Ethylbenzene, however, is also produced in these catalytic processes. U.S. Pat. No. 4,115,424 and U.S. Pat. No. 4,140,726 describe a catalytic process using toluene and formaldehyde with molecular sieve catalysts of the X or Y zeolite structure containing cesium, rubidium or potassium cations and boron or phosphorous, but this process also produces large amounts of ethylbenzene. These and other drawbacks of the prior art are overcome by the process described herein.

SUMMARY OF THE INVENTION

Styrene is produced from toluene and formaldehyde by contacting a gas comprised of toluene and formaldehyde with the formaldehyde being 0.001 to 0.10 mole per 1 mole of toluene with a catalyst comprised of a basic compound selected from the group consisting of the oxides and hydroxides and mixtures thereof of metals of lithium, sodium, potassium, rubidium, cesium, magnesium, calcium, strontium, barium and mixtures thereof at a temperature of from 250° C. to 450° C. at a pressure of from 0.1 atmosphere to 10 atmospheres, and at a volumetric space velocity of from 100 to 5000 reciprocal hours (hr.$^{-1}$)

DESCRIPTION OF THE INVENTION a. General Description

Styrene is a commodity chemical sold and utilized in extremely large volumes for producing polystyrene and other products. Hence, any process for producing styrene is of great interest if it offers a potential advantage in cost or availability of reactant materials. Toluene and formaldehyde are potentially attractive materials for the production of styrene, and the present invention provides an improved process for producing styrene from toluene and formaldehyde.

In the present invention, the process has improved selectivity to the desired styrene because it was discovered that certain ratios of toluene to formaldehyde are required whereby the ethylbenzene production is reduced to a very low amount and the selectivity to the formation of styrene is increased over that of the known prior art processes.

In general, the catalysts are those described and known in the prior art but which are supported on refractory-type oxide. Refractory-type oxides such as silica, alumina, titanium, silica, alumina, carbon, magnesium oxides and zeolites may also be used.

Because it is known to those skilled in the art, it is preferable to support the catalyst to increase its surface area, which can be from 5 sq. meters per gram to 300 square meters per gram or more. Preferably, the surface area is from 10 to 200m$^2$/gram. Supports can be refractory oxides mentioned herein upon which the active catalysts compositions are deposited, see for example Emmet's Treatise on Catalysis, or incorporated therein as described herein. The supports can be zeolites in which the Group I or II elements are based exchanged. Thus, a process is provided which gives improved selectivity to styrene while keeping the ethylbenzene products low and in some cases almost non-existent. Also, the process forms only carbon monoxide or carbon dioxide or other products which are readily separated from the reaction and/or can be recycled for further conversion to styrene.

For production of styrene without large amounts of ethyl benzene, the catalystic process employs conditions generally used in alkylation reactions, such as those used in the methylation of toluene with other zeolite or refractory oxide-type catalysts, with the selection of particular conditions being influenced by such considerations as activity and temperature stability of the particular catalyst, the desired conversion and the attainable product selectivity. The temperatures appropriate for the reactions of toluene and formaldehyde for the formation of styrene are, for example, about 250° C. to 450° C. Preferably the temperature range is from 300° C. to 400° C., with the range of 325° C. to 375° C. being most preferred. It is better to use the lower temperatures rather than the higher temperatures so as to maintain high selectivity for styrene formation. Because separation of ethylbenzene from styrene presents a problem, keeping the concentration of ethylbenzene low makes the separation of styrene from the other products economical and, in fact, as will be seen herein no separation from ethylbenzene is essentially needed and the styrene is almost pure styrene.

The reactants of toluene and formaldehyde can be brought into contact with the catalyst in the usual manner generally as a stream of reactants conducted over or through a bed of catalysts. The contact time can be varied over a wide range but will generally be selected to obtain an acceptable conversion at the reaction temperature. For example ranges of gas hourly space velocities from 100–5,000 reciprocal hours (hr.$^{-1}$) or more are operable, and good conversions can often be obtained even at reasonably high space velocities such as from 500–1,500 reciprocal hours or so. The reaction in general will occur as long as the quantities of both formaldehyde and toluene are present in ranges, for example, of about 0.0001 to 0.10 mole of formaldehyde per 1 mole of toluene, and preferably from 0.01 to 0.05 mole of formaldehyde per 1 mole of toluene.

The methylations of toluene from the reaction of formaldehyde with the catalyst under the process conditions can produce formaldehyde decomposition products, such as dimethyl ether, carbon monoxide and carbon dioxide. This differs from the prior art processes which form various xylenes, other alkylated aromatics, polymers, other aromatics and coke materials along with styrene and ethylbenzene. The present invention produces primarily styrene. It is obvious that there is an economic advantage when the desired product forms without waste or less desired product. The use of the present process increases the selectivity to styrene, that is, it increases the amount of styrene obtained per unit of formaldehyde which has reacted.

In the process of the present invention, the catalysts described herein have a basic compound within the catalyst which may be one or more of the Group I or Group II metal oxides in the form of its hydroxide, or mixtures thereof listed herein. The ratio of the mixtures thereof may be anywhere from 1 to 1,000 parts by weight of a single Group I or II metal together with one or more of the other Group I or II metals. It is not necessary that the metal of Group I be solely in the form of a mono oxide but may be as a mixture of mono oxides or dioxides as described herein, in which a small amount of hydroxide may exist under the process conditions, as known to those skilled in the art.

In general the surface area of the catalyst used herein varies from 5 to 300 square meters per gram, but preferably it is within the range of from 10 to 200 square meters per gram.

The amount of the basic compound is from 1 to 50 weight percent, but preferably from ten to 30 weight percent.

GENERAL DESCRIPTION OF THE CATALYST

The catalyst is a Group I and Group II oxide which may under the reaction conditions have some hydroxide therein and be dispersed on refractory supports such as silica, alumina, titania, or other refractory supports mentioned herein and known to those skilled in the art. See, for example, Emmett's Treatise on Catalysis. It is more preferred to use a refractory oxide support because these are able to withstand the heat of the reaction and prevent sintering and migration of the catalytic components thereon as well as to provide a more stable catalyst so that long lifetime is observed.

The preferred salts for the basic components are the hydroxides of Li, Na, K, Rb, Cs, Mg, Ca, Sr and Ba although barium nitrate is also suitable. In general, the nitrate or chloride salts of the basic components are not preferred. Cesium hydroxide is the most preferred salt.

The methods of incorporating the catalytic components are not unique and are familiar to those skilled in the art. They are generally described in the following references:

Acres, G. J. K, Bird, A. J., Jeulsens, J. W. and King, F in Catalysis, A Specialist Periodical Report, C. Kimball and D. A. Dowden, eds. Vol. 4, pp. 1–29, The Royal Society of Chemistry, Burlington House, London, 1980, Anderson, J. R. "Structure of Metallic Catalysts" pp. 451–458, Academic Press, N.Y., 1975, which references are incorporated herein.

EXAMPLES OF THE CATALYSTS

All the base supported catalysts were prepared by dissolving a soluble salt in water and adding the solution to $SiO_2$ (300 $M^2/g$) with mixing. The resulting samples were then generally dried several hours in air at 110–120° C. and calcined in air or helium at 450° C. for four hours. All base catalysts were prepared at a concentration of 2 mmole base element per gram of support. The Table below describes specific aspects of the preparations.

| Element | Salt Used | Support |
|---|---|---|
| Cs | CsOH, 8.15 g. | $SiO_2$, 20.39 g. |
| K | KOH, 2.06 g. | $SiO_2$, 18.31 g. |
| Ba | $Ba(NO_2)_2$, 9.39 g. | $SiO_2$, 20.47 g. |
| Ca | $Ca(OH)_2$, 2.90 g. | $SiO_2$, 19.56 g. |

A RbX zeolite was prepared according to the methods described by Unland, M. (J. Phys. Chem., 82 580, 1978) which is incorporated herein. Rubidium chloride was exchanged with Linde 13X zeolite followed by washing to remove chloride ion, and drying for 5 hours at 110–120° C. in air. The exchange procedure gave about 70% exchange for Rb.

The Group I and II elements may exist either as oxides or dioxides or other metastable oxides with some hydroxide being present in the working state of the catalyst. As known to those skilled in the art, the actual oxidation state at reaction conditions is difficult to know. Consequently as used herein and in the claims, the terms "oxide" and "hydroxide" as used herein and in the claims refers to any of the oxides or hydroxides of the Group I or II elements claimed and/or described herein.

The prepared catalysts were charged to the reactor and pre-treated by heating in a flow of helium (1200 hr.$^{-1}$) to 450° C. over a 2 hour period followed by a 1 hour treatment in flowing helium at 450° C. Subsequently, the reactor temperature was set at that for the catalytic test and the flow of reactants initiated over the catalyst.

b. Examples of Catalyst Tests/Toluene-Formaldehyde

That a critical range of toluene to formaldehyde mole ratio is critical for achieving selective conversion to styrene without ethylbenzene formation is demonstrated by the following experiments. A $CsOH/s_iO_2$ catalyst (24% wt CsOH) was prepared as previously described. The catalyst was charged to a fixed-bed catalytic reactor and pretreated in flowing helium at 350° C. for several hours. A series of experiments at constant temperature, 350° C., and varying toluene to formaldehyde mole ratios was carried out. At each feed ratio, five milliters of liquid feed was passed over the catalyst to establish a steady state and then the feed rate reduced to a rate of 500 hr$^{-1}$. Formaldehyde was fed to the reactor as the trimer, 1,3,5 trioxane, because of convenience of handling at the reaction conditions used. The trioxane decomposes to the desired formaldehyde reactant.

The following table gives the results of the tests:

| $CH_2O$ in Toluene (Mole %) | Styrene Selectivity (Mole % on $CH_2O$) | Styrene Yield (Mole % on $CH_2O$) |
|---|---|---|
| 1 | 11.6 | 10 |
| 2.5 | 5.7 | 4 |
| 5 | 4 | 2.8 |
| 10 | 2.4 | 1.5 |
| 25 | 0.6 | 0.4 |

Clearly high selectivity and yield to styrene, without ethylbenzene formation are favored by operation at toluene/formaldehyde mole ratios greater than 95/5.

While the invention has been described with reference to specific details of certain illustrative embodiments, it is not intended that it shall be limited thereby except insofar as such details appear in the accompanying claims.

We claim:

1. A process of producing styrene from toluene and formaldehyde which comprises:

Contacting a gas comprised of toluene and formaldehyde, the formaldehyde being from 0.001 to 0.10 mole per one mole toluene with a catalyst comprised of a basic compound selected from the group consisting of an oxide and hydroxide, and mixtures thereof, of a metal selected from the group consisting of lithium, sodium, potassium, rubidium, cesium, magnesium, calcium, strontium, barium and mixtures thereof, at a temperature of from 250° C. to 450° C., at a pressure of from 0.1 atmosphere to 10 atmospheres, and at a volumetric space velocity of from 100 to 5000 reciprocal hours ($hr.^{-1}$).

2. The process is recited in claim 1 wherein the mole ratio of formaldehyde to toluene is from 0.01 to 0.05 mole of formaldehyde to one mole of toluene.

3. The process is recited in claim 2 wherein the basic compound metal is cesium.

4. The process as recited in claim 3 wherein the temperature range is from 325° C. to 375° C.

* * * * *